US00PP11536P

United States Patent [19]

Meier et al.

[11] Patent Number: Plant 11,536

[45] Date of Patent: Oct. 3, 2000

[54] KENTUCKY BLUEGRASS DESIGNATED 'BA87-102'

[75] Inventors: Virgil D. Meier, Marysville, Ohio; Jay B. Burr, SE. Salem, Oreg.

[73] Assignee: OMS Investments, Inc., Wilmington, Del.

[21] Appl. No.: 09/032,057

[22] Filed: Feb. 27, 1998

[51] Int. Cl.[7] ..... A01H 5/00

[52] U.S. Cl. ..... Plt./393

[58] Field of Search ..... Plt./393

[56] References Cited

U.S. PATENT DOCUMENTS

| | | | |
|---|---|---|---|
| P.P. 3,150 | 5/1972 | Pepin et al. | Plt./393 |
| P.P. 3,156 | 5/1972 | Fuchigami et al. | Plt./393 |
| P.P. 3,186 | 5/1972 | Barenbrug et al. | Plt./393 |
| P.P. 4,336 | 11/1978 | Mayer et al. | Plt./393 |
| P.P. 6,280 | 9/1988 | Meier et al. | Plt./393 |
| P.P. 6,537 | 1/1989 | Meier et al. | Plt./393 |
| P.P. 6,538 | 1/1989 | Meier et al. | Plt./393 |
| P.P. 6,585 | 2/1989 | Meier et al. | Plt./393 |
| P.P. 7,831 | 3/1992 | Meier et al. | Plt./393 |
| P.P. 8,490 | 12/1993 | Meier et al. | Plt./393 |
| P.P. 9,036 | 1/1995 | Meier et al. | Plt./393 |
| P.P. 9,209 | 7/1995 | Mayer | Plt./393 |
| P.P. 9,611 | 7/1996 | Meier | Plt./393 |
| P.P. 9,848 | 4/1997 | Meier et al. | Plt./393 |
| P.P. 9,977 | 7/1997 | Meier et al. | Plt./393 |
| P.P. 10,080 | 10/1997 | Meier et al. | Plt./393 |
| P.P. 10,081 | 10/1997 | Meier et al. | Plt./393 |

*Primary Examiner*—Lynette R. F. Smith
*Assistant Examiner*—Wendy A Baker
*Attorney, Agent, or Firm*—Jones, Day, Reavis & Pogue

[57] ABSTRACT

A variety of Kentucky bluegrass having a medium level of resistance to melting out, brownpatch, crown rust, summer patch and powdery mildew; a medium green color throughout the growing season, the ability to form a medium to high quality, dense turf under a variety of environmental conditions; relatively short and heavy seeds and a high level of seed yielding capacity.

3 Drawing Sheets

BACKGROUND OF THE INVENTION

Field of the Invention

The present invention relates to a new and distinct variety of *Poa pratensis* that has been designated 'Ba87-102' Kentucky Bluegrass.

Description of Related Art

Kentucky Bluegrasses have been disclosed in U.S. Plant Pat. No. 3,156, issued May 9, 1972; U.S. Plant Pat. No. 3,186, issued May 23, 1972; U.S. Plant Pat. No. 4,336, issued Nov. 28, 1978: U.S. Plant Pat. No. 6,280, issued Sep. 6, 1988; U.S. Plant Pat. Nos. 6,537 and 6,538, issued on Jan. 17, 1989; U.S. Plant Pat. No. 6,585, issued Feb. 7, 1989; U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995; U.S. Plant Pat. No. 9,209, issued Jul. 18, 1995; U.S. Plant Pat. No. 9,611, issued Jul. 23, 1996; U.S. Plant Pat. No. 9,848, issued Apr. 1, 1997: U.S. Plant Pat. No. 9,977, issued Jul. 22, 1997; U.S. Plant Pat. No. 10,080, issued Oct. 21, 1997; U.S. Plant Pat. No. 10,081, issued Oct. 21, 1997; U.S. Plant Pat. No. 10,384, issued May 5, 1998; and U.S. Plant Pat. No. 10,925, issued May 25, 1999.

SUMMARY OF THE VARIETY

'Ba87-102' plant material originated as an open pollinated progeny of 'Ba74-331' as the seed parent. 'Ba74-331' is a Kentucky Bluegrass plant grown and maintained in a plant nursery at The Scotts Company in Marysville, Ohio. The pollen parent of 'Ba87-102' Kentucky Bluegrass is unknown. As a result of this breeding, a distinct variety was produced and asexually propagated by rhizomes, tillers and disseminules. Seed of 'Ba87-102' Kentucky Bluegrass was produced first at Marysville, Ohio, and later at Gervais, Oreg. This seed was used to plant turf performance evaluation trials and later seed production fields.

Asexual reproduction of 'Ba87-102' by propagules (tillers and rhizomes) and by disseminules (modified caryopses produced by apomixis) has consistently produced progeny plants indistinguishable from a mother plant. The apomixis level of 'Ba87-102' is approximately 98% based upon examining seedling characteristics of approximately 100 to 150 seedlings from different crop years in a growth chamber.

'Ba87-102' has a number of desirable characteristics, including a high seed yield and a low seed count per pound, both of which are valuable traits in seed production. 'Ba87-102' has an attractive leafy, dense turf type, moderately narrow leaf blade and a medium green color which can be maintained throughout the entire growing season. 'Ba87-102' demonstrates good spring greening and good winter color under mild winter conditions.

In comparison with a number of other Kentucky Bluegrass varieties, 'Ba87-102' has a significantly shorter seed and longer rachilla than several other Kentucky Bluegrasses and a significantly lower seed count per pound than several other Kentucky Bluegrasses. The panicle of 'Ba87-102' Kentucky Bluegrass is generally longer, but approximately average in whorl number and branch counts per whorl when compared to several other Kentucky Bluegrasses. 'Ba87-102' has, on average, more narrow spikelets, and a lower number of florets per spikelet. The flag leaf ligule is of average length and generally has more hairs on the ligule than the other Kentucky bluegrass varieties that were examined. The flag leaf of 'Ba87-102' was generally longer, and significantly thinner than the other varieties. 'Ba87-102''s peduncle is significantly shorter, but its width is about average. The top internode of the culm is generally shorter than average. The vegetative leaf is below average in length and width and slightly below average in thickness. The ligule of the vegetative leaf is significantly longer than various other Kentucky bluegrasses. 'Ba87-102' has significantly fewer hairs on the upper ligule margin and collar margin than many of the Kentucky bluegrass varieties and signficantly more hairs of the leaf sheath margin and fewer hairs on the leaf sheath dorsal than other Kentucky bluegrasses.

DETAILED DESCRIPTION OF THE VARIETY

Figure 1:
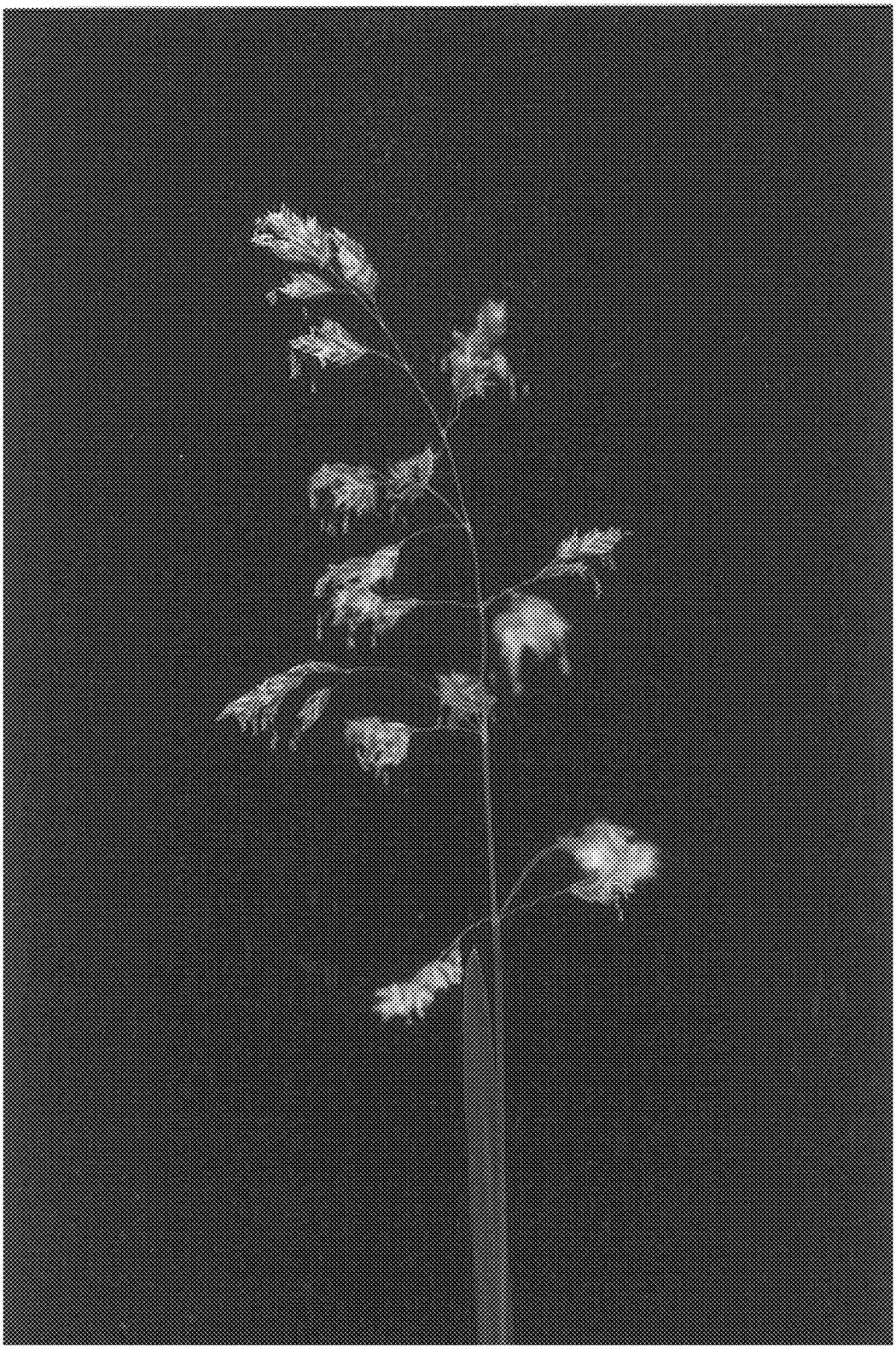
FIG. 1 is a 'Ba87-102' Kentucky bluegrass panicle.
Figure 2:
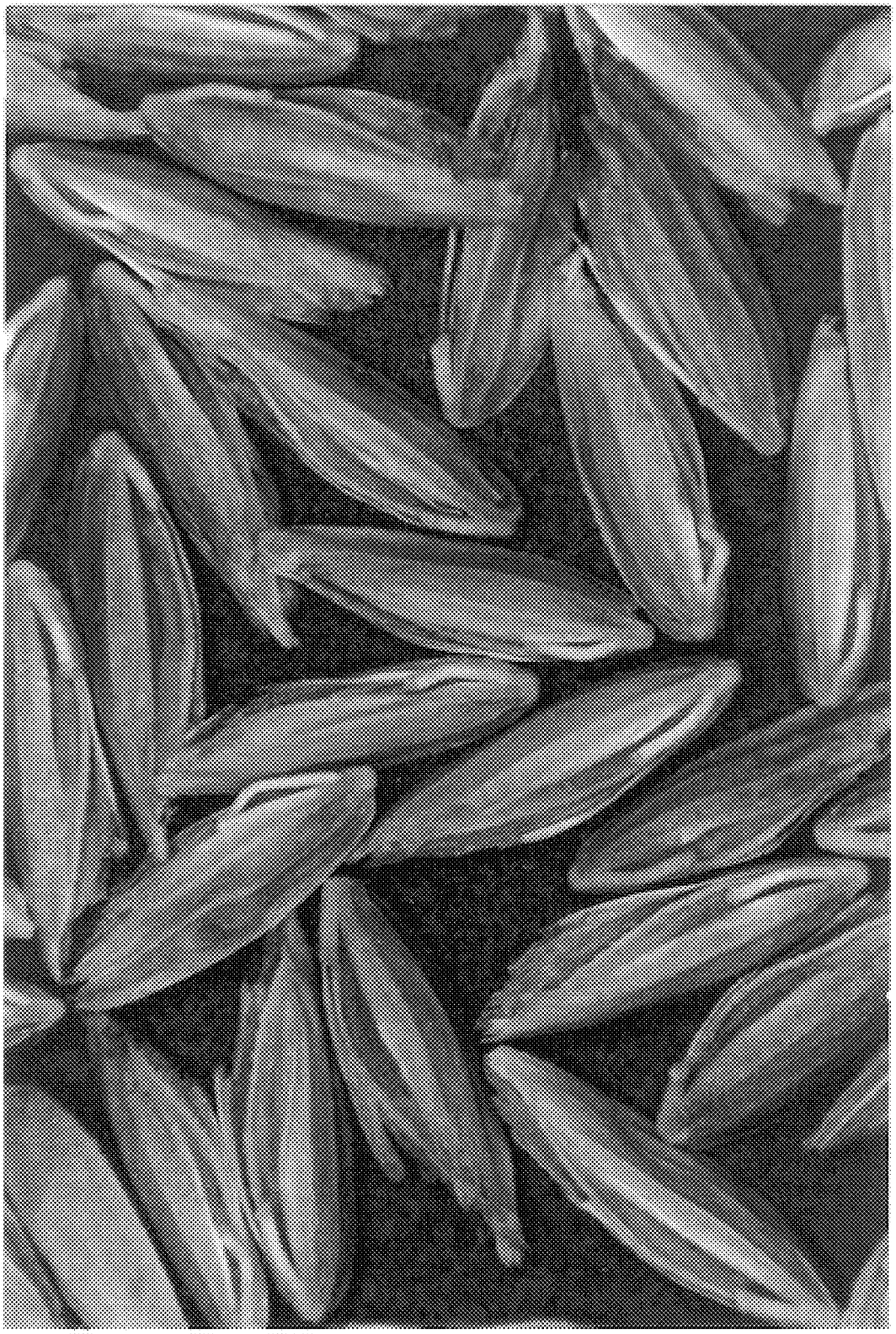
FIG. 2 is a 'Ba87-102' Kentucky bluegrass seed.
Figure 3:
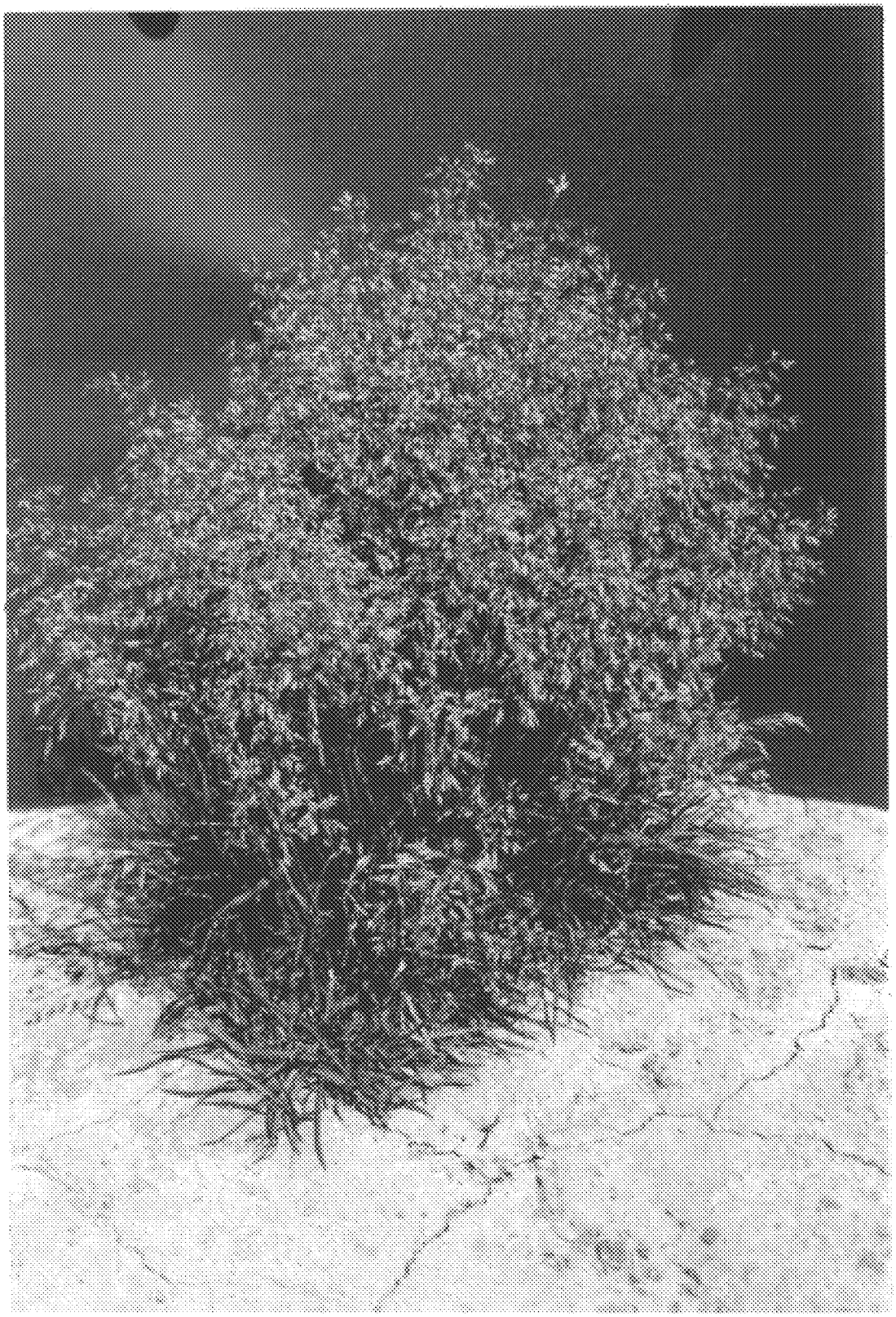
FIG. 3 is an unmowed 'Ba87-102' Kentucky bluegrass plant shortly after completing anthesis in June.

'Ba87-102' Kentucky bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60–80° F.), culms are erect averaging 43.05 cm in length. The uppermost internode averages 7.44 cm in length. The peduncle averages 19.26 cm in length and 0.89 mm in width. The vegetative leaf averages 20.80 cm in length, 3.89 mm in width, 0.19 mm in thickness and the ligule 0.40 mm in length. The vegetative leaf generally has more hairs on the margins of the leaf sheath and fewer hairs on the collar compared to other varieties. The flag leaf averages 7.11 cm in length, 3.21 mm in width, 0.089 mm in thickness and a ligule length of 1.00 mm. The panicle averages 10.25 cm in length, 6.63 cm in width, and has 5.7 whorls with the lowest whorl and the third whorl from the bottom of the panicle averaging 3.6 and 3.5 branches, respectively. A spikelet in the lowest whorl averages 4.71 mm in length, 1.69 mm in width, 3.0 florets and the outer glume and inner glume average 2.65 mm and 3.41 mm in length, respectively. A spikelet from the third whorl from the bottom of the panicle averages 4.96 mm in length, 1.89 mm in width, 3.6 florets, and the outer glume and inner glume average 3.07 mm and 3.70 mm in length, respectively.

'Ba-87-102' differs significantly from several of the other Kentucky bluegrass varieties in regard to such morphological characteristics as peduncle length, culm length, top internode length, vegetative leaf length, vegetative leaf width, vegetative leaf thickness, hairs on vegetative leaf sheath margin, hairs on vegetative leaf ligule upper margin, hairs on vegetative leaf collar margin, flag leaf length, flag leaf thickness, panicle length, spikelet width, outer glume length, and inner glume length.

Since environmental conditions such as soil and climate may influence morphological characteristics to some extent, comparisons of 'Ba87-102' were made with other Kentucky bluegrass varieties under like conditions and the comparisons are set forth in Tables 1–7 as follows:

TABLE 1

Morphological Comparisons of Peduncles, Culms, and Top Internodes of 'Ba87-102' and Other Kentucky Bluegrass Varieties in the Greenhouse at Marysville, Ohio.

| Variety | Peduncle Length (cm) | Peduncle Width (mm) | Culm Length (cm) | Top Internode Length (cm) |
|---|---|---|---|---|
| 'Ba87-102' | 19.26 | 0.89 | 43.05 | 7.44 |
| 'Abbey' | 26.83 | 0.99 | 33.30 | 7.40 |
| 'Ascot' | 18.76 | 0.67 | 38.25 | 5.79 |

TABLE 1-continued

Morphological Comparisons of Peduncles, Culms, and Top Internodes of 'Ba87-102' and Other Kentucky Bluegrass Varieties in the Greenhouse at Marysville, Ohio.

| Variety | Peduncle Length (cm) | Peduncle Width (mm) | Culm Length (cm) | Top Internode Length (cm) |
|---|---|---|---|---|
| 'Famous' | 20.99 | 1.04 | 48.88 | 8.85 |
| 'Nottingham' | 26.70 | 1.19 | 39.20 | 9.42 |
| 'Raven' | 26.12 | 0.78 | 55.32 | 11.64 |
| 'Sidekick' | 27.22 | 0.91 | 55.88 | 10.36 |
| LSD (.05) | 2.76 | 0.11 | 3.64 | 1.56 |

TABLE 2

Morphological Comparisons of Vegetative Leaves of 'Ba87-102' and Other Kentucky Bluegrass Varieties in the Greenhouse at Marysville, Ohio.

| Variety | Length (cm) | Width (mm) | Thickness (mm) | Ligule Length (mm) |
|---|---|---|---|---|
| 'Ba87-102' | 20.80 | 3.89 | 0.19 | 0.40 |
| 'Abbey' | 23.42 | 4.02 | 0.20 | 0.40 |
| 'Ascot' | 28.41 | 3.84 | 0.19 | 0.31 |
| 'Famous' | 27.46 | 4.58 | 0.21 | 0.41 |
| 'Nottingham' | 26.46 | 4.78 | 0.20 | 0.40 |
| 'Raven' | 24.44 | 4.62 | 0.21 | 0.37 |
| 'Sidekick' | 29.03 | 4.94 | 0.21 | 0.48 |
| LSD (.05) | 3.54 | 0.45 | 0.01 | 0.05 |

TABLE 3

Morphological Comparisons of the Level of Hairs on the Vegetative Leaves of 'Ba87-102' and Other Kentucky Bluegrass Varieties in the Greenhouse at Marysville, Ohio.

| Variety | Leaf Sheath Margin | Leaf Sheath Dorsal | Ligule Upper Margin | Collar Margin | Leaf Dorsal |
|---|---|---|---|---|---|
| 'Ba87-102' | 3.40 | 1.0 | 4.6 | 2.2 | 1.0 |
| 'Abbey' | 3.10 | 2.7 | 6.3 | 3.6 | 1.0 |
| 'Ascot' | 2.10 | 1.0 | 2.0 | 4.4 | 0.0 |
| 'Famous' | 2.80 | 1.4 | 4.3 | 3.3 | 1.0 |
| 'Nottingham' | 3.30 | 3.6 | 7.1 | 4.4 | 1.0 |
| 'Raven' | 1.80 | 1.1 | 3.1 | 2.1 | 1.0 |
| 'Sidekick' | 2.10 | 1.2 | 2.3 | 3.6 | 0.0 |
| LSD (.05) | 0.55 | 0.4 | 0.7 | 0.7 | 0.1 |

Rating Scale: 0–9, 0 = None; 9 = Many.

TABLE 4

Morphological Comparisons of Flag Leaves of 'Ba87-102' and Other Kentucky Bluegrass Varieties in the Greenhouse at Marysville, Ohio.

| Variety | Length (cm) | Width (mm) | Thickness (mm) | Ligule Length (mm) | Ligule Hair* |
|---|---|---|---|---|---|
| 'Ba87-102' | 7.11 | 3.21 | 0.089 | 1.00 | 2.00 |
| 'Abbey' | 3.57 | 2.99 | 0.109 | 0.91 | 1.60 |
| 'Ascot' | 6.03 | 2.49 | 0.102 | 1.15 | 1.60 |
| 'Famous' | 7.65 | 3.83 | 0.102 | 1.19 | 1.38 |
| 'Nottingham' | 4.77 | 3.71 | 0.124 | 1.08 | 2.30 |
| 'Raven' | 5.87 | 3.38 | 0.104 | 1.08 | 1.20 |
| 'Sidekick' | 6.65 | 3.61 | 0.104 | 1.07 | 1.10 |
| LSD (.05) | 1.13 | 0.47 | 0.013 | 0.16 | 0.49 |

*Rating Scale: 0–9; 0 = None, 9 = Many.

TABLE 5

Morphological Comparisons of Panicles, Whorl Number and Whorl Branches of 'Ba87-102' and Other Kentucky Bluegrass Varieties in the Greenhouse at Marysville, Ohio.

| | Panicle | | Number of Branches | | |
|---|---|---|---|---|---|
| Variety | Length (cm) | Width (cm) | Whorl No. | Lowest Whorl | Third Whorl |
| 'Ba87-102' | 10.25 | 6.63 | 5.7 | 3.6 | 3.5 |
| 'Abbey' | 6.04 | 4.99 | 5.8 | 3.7 | 3.3 |
| 'Ascot' | 10.03 | 7.01 | 4.2 | 2.2 | 2.0 |
| 'Famous' | 12.11 | 8.11 | 6.2 | 4.2 | 3.8 |
| 'Nottingham' | 8.08 | 7.15 | 7.0 | 4.4 | 4.4 |
| 'Raven' | 8.15 | 6.36 | 5.3 | 4.0 | 3.2 |
| 'Sidekick' | 11.22 | 3.52 | 5.5 | 2.8 | 2.6 |
| LSD (.05) | 0.92 | 1.21 | 0.6 | 0.6 | 0.5 |

TABLE 6

Morphological Comparisons of Spikelets and Florets of 'Ba87-102' and Other Kentucky Bluegrass Varieties in the Greenhouse at Marysville, Ohio.

| | Spikelet | | | | Number of Florets per Spikelet | |
|---|---|---|---|---|---|---|
| | Lowest Whorl | | Third Whorl | | | |
| Variety | Length (mm) | Width (mm) | Length (mm) | Width (mm) | Lowest Whorl | Third Whorl |
| 'Ba87-102' | 4.71 | 1.69 | 4.96 | 1.89 | 3.0 | 3.6 |
| 'Abbey' | 4.67 | 1.85 | 4.54 | 1.94 | 3.1 | 3.1 |
| 'Ascot' | 5.34 | 2.03 | 5.10 | 2.06 | 3.2 | 2.9 |
| 'Famous' | 5.19 | 2.14 | 5.18 | 2.09 | 4.0 | 3.9 |
| 'Nottingham' | 5.69 | 2.33 | 5.22 | 2.47 | 4.4 | 3.7 |
| 'Raven' | 4.63 | 2.12 | 4.75 | 2.04 | 3.9 | 3.8 |
| 'Sidekick' | 5.08 | 2.67 | 5.23 | 2.71 | 4.1 | 4.6 |
| LSD (.05) | 0.49 | 0.30 | 0.43 | 0.36 | 0.6 | 0.6 |

TABLE 7

Morphological Comparisons of Glume Size of 'Ba87-102' and Other Kentucky Bluegrass Varieties in the Greenhouse at Marysville, Ohio.

| | Outer Glume | | | | Inner Glume | | | |
|---|---|---|---|---|---|---|---|---|
| | Lowest Whorl | | Third Whorl | | Lowest Whorl | | Third Whorl | |
| Variety | Length (mm) | Width (mm) | Length (mm) | Width (mm) | Length (mm) | Width (mm) | Length (mm) | Width (mm) |
| 'Ba87-102' | 2.65 | 0.51 | 3.07 | 0.62 | 3.41 | 0.76 | 3.70 | 0.81 |
| 'Abbey' | 2.51 | 0.53 | 2.52 | 0.46 | 2.96 | 0.69 | 3.00 | 0.69 |
| 'Ascot' | 3.92 | 0.50 | 3.74 | 0.56 | 4.13 | 0.71 | 4.03 | 0.68 |
| 'Famous' | 2.99 | 0.56 | 2.91 | 0.64 | 3.38 | 0.74 | 3.36 | 0.73 |
| 'Nottingham' | 2.99 | 0.61 | 2.91 | 0.57 | 3.31 | 0.81 | 3.33 | 0.67 |
| 'Raven' | 2.85 | 0.53 | 2.87 | 0.47 | 3.11 | 0.74 | 3.09 | 0.68 |
| 'Sidekick' | 3.27 | 0.52 | 3.41 | 0.63 | 3.51 | 0.65 | 3.69 | 0.73 |
| LSD (.05) | 0.31 | 0.10 | 0.30 | 0.11 | 0.29 | 0.14 | 0.28 | 0.12 |

The conditioned seed of 'Ba87-102' averages 2.80 mm in length, 0.75 mm in width, and a rachilla length of 0.81 mm. It has a low level of hairs at the base of the lemma. 'Ba87-102' has approximately 942,700 seeds per pound which indicates that its seeds are significantly heavier than most varieties. 'Ba87-102' differs signficantly from several of the other Kentucky bluegrass varieties in regard to seed characteristics including length, lemma hairs and number of seeds per pound. Comparisons of 'Ba87-102' with other Kentucky bluegrass varieties in terms of seed measurements and seed numbers per pound are shown in Tables 8 and 9 as follows:

TABLE 8

Morphological Comparisons of Seed Length, Width, Rachilla Length, and Lemma Hairs of 'Ba87-102' with Other Kentucky Bluegrass Varieties After Conditioning.

| Variety | Length (mm) | Width (mm) | Rachilla (mm) | Lemma Hairs[1/] |
|---|---|---|---|---|
| 'Ba87-102' | 2.80 | 0.75 | 0.81 | 1.22 |
| 'Abbey' | 3.02 | 0.85 | 0.56 | 1.80 |

TABLE 8-continued

Morphological Comparisons of Seed Length, Width, Rachilla Length, and Lemma Hairs of 'Ba87-102' with Other Kentucky Bluegrass Varieties After Conditioning.

| Variety | Length (mm) | Width (mm) | Rachilla (mm) | Lemma Hairs[1/] |
|---|---|---|---|---|
| 'Ascot' | 3.00 | 0.81 | 0.68 | 6.30 |
| 'Famous' | 3.02 | 0.86 | 0.65 | 1.56 |
| 'Nottingham' | 3.02 | 0.84 | 0.69 | 1.10 |
| 'Raven' | 2.88 | 0.80 | 0.67 | 2.50 |
| 'Sidekick' | 2.84 | 0.84 | 0.88 | 2.11 |
| LSD (.05) | 0.20 | 0.11 | 0.21 | 0.70 |

[1/]Rating Scale 0–9; 9 = most hairs

TABLE 9

Comparison of Seeds Per Pound of 'Ba87-102' and Other Kentucky Bluegrass Varieties After Conditioning.

| Variety | Seeds per Pound |
|---|---|
| 'Ba87-102' | 942,700 |
| 'Abbey' | 1,003,000 |
| 'Ascot' | 1,039,400 |
| 'Coventry' | 1,374,700 |
| 'Famous' | 1,128,600 |
| 'Misty' | 1,127,400 |
| 'Nottingham' | 1,066,000 |
| 'Raven' | 1,127,100 |
| 'Sidekick' | 928,000 |
| LSD (.05) | 38,080 |

'Ba87-102' has performed well under different environmental conditions, in different climatic zones in the United States, and under different management regimes as exhibited by medium to high turf quality ratings in comparison with other Kentucky bluegrass varieties. In addition, it has a medium green color which can be maintained throughout the growing season.

With regard to a comparative analysis conducted for purposes of determining color of 'Ba87-102' plants relative to other Kentucky bluegrass varieties, readings were taken of the vegetative color of 'Ba-87-102' during mid-October while the mowed turf was actively growing with adequate nutrient and water availability. The readings were taken in full sun with several actively growing leaves being compared, one at a time, utilizing color chips from the Munsell Book of Color as a reference. On this basis, the color of 'Ba87-102' was determined to be 5 GY 4/6. During the same time period, the color of similar leaves of other Kentucky bluegrass varieties were determined by the same procedure to be as follows: 'Ascot'-5 GY 4/4; 'Buckingham'-7.5 GY 4/4; 'Ba77-700'-5 GY 4/6; 'Midnight'-7.5 GY 4/4; 'Abbey'-5 GY 4/6; and 'Victa'-5 GY 4/4. However, it should be noted that the general apparent color of turf does not always correlate directly with the color of the individual actively growing leaves within the turf and that turf color varies with nutrient level, water availability and time of year, age of plant, maturity of plant, level of disease and mowing history, with some varieties being darker or lighter green, depending on such factors.

In addition to color, two other important components involved in judging the overall quality of turf are turf density and leaf texutre. 'Ba87-102' is comparable to other improved varieties for turf density throughout the growing season, and has finer leaf texture in a turf situation than many other improved varieties.

Comparisons of 'Ba87-102' with other Kentucky bluegrass varieties for quality, genetic color, spring greenup, fall and winter color, turf density, and leaf texture are shown in Tables 10–15 as follows:

TABLE 10

A Comparison of Quality of 'Ba87-102' and Other Kentucky Bluegrass Varieties as Affected by Environmental Conditions.

| Variety | Dense Shade[1/] | Full Sun[2/] |
|---|---|---|
| 'Ba87-102' | 4.7 | 5.6 |
| 'Abbey' | 4.2 | 5.6 |
| 'Ascot' | 5.4 | 5.6 |
| 'Conventry' | 5.1 | 5.9 |
| 'Chateau' | 5.3 | 6.0 |
| 'Classic' | 4.7 | 5.8 |
| 'Eclipse' | 4.6 | 5.8 |
| 'Glade' | 4.4 | 6.0 |
| 'Kenblue' | 3.2 | 4.9 |
| 'Limousine' | 4.8 | 6.0 |
| 'Midnight' | 3.2 | 6.3 |
| 'Raven' | 3.4 | 5.7 |
| 'Sidekick' | 4.3 | 5.1 |
| LSD (.05) | 1.6 | 0.2 |

Rating Scale: 0–9, 9 = Excellent
[1/]From Maryland
[2/]From 28 different locations in the US

TABLE 11

A Comparison of Quality of 'Ba87-102' and Other Kentucky Bluegrass Varieties as Affected by Climatic Zones.

| Variety | Transition Zone[1/] | Cool Arid[2/] | Cool Humid[3/] |
|---|---|---|---|
| 'Ba87-102' | 5.5 | 5.6 | 5.7 |
| 'Abbey' | 5.4 | 5.7 | 5.7 |
| 'Ascot' | 5.2 | 5.6 | 5.8 |
| 'Coventry' | 5.7 | 5.5 | 6.2 |
| 'Chateau' | 5.7 | 6.0 | 6.1 |
| 'Classic' | 5.3 | 6.0 | 6.1 |
| 'Eclipse' | 5.5 | 5.5 | 6.0 |
| 'Glade' | 5.8 | 6.1 | 6.1 |
| 'Kenblue' | 4.8 | 6.1 | 4.9 |
| 'Limousine' | 5.7 | 5.3 | 6.3 |
| 'Midnight' | 6.1 | 6.3 | 6.5 |
| 'Raven' | 5.6 | 5.6 | 5.8 |
| 'Sidekick' | 5.0 | 5.4 | 5.1 |
| LSD (.05) | 0.3 | 0.5 | 0.2 |

Rating Scale: 0–9, 9 = Excellent
[1/]From 10 different locations in the US
[2/]From 3 different locations in the US
[3/]From 16 different locations in the US

TABLE 12

A Comparison of Quality of 'Ba87-102' and Other Kentucky Bluegrass Varieties as Affected by Mowing Height.

| | Mowing Height | |
|---|---|---|
| Variety | 1.1–1.5[1/] (in.) | 2.1–3.0[2/] (in.) |
| 'Ba87-102' | 5.2 | 6.2 |
| 'Abbey' | 5.1 | 6.1 |
| 'Ascot' | 5.3 | 5.8 |
| 'Coventry' | 5.5 | 6.5 |
| 'Chateau' | 5.5 | 6.4 |
| 'Classic' | 5.1 | 6.5 |
| 'Eclipse' | 5.4 | 6.2 |

TABLE 12-continued

A Comparison of Quality of 'Ba87-102' and Other Kentucky Bluegrass Varieties as Affected by Mowing Height.

| Variety | Mowing Height 1.1–1.5[1/] (in.) | 2.1–3.0[2/] (in.) |
|---|---|---|
| 'Glade' | 5.7 | 6.0 |
| 'Kenblue' | 4.2 | 6.0 |
| 'Limousine' | 5.4 | 6.7 |
| 'Midnight' | 6.2 | 6.3 |
| 'Raven' | 5.3 | 6.4 |
| 'Sidekick' | 4.4 | 5.6 |
| LSD (0.5) | 0.3 | 0.4 |

Rating Scale: 0–9, 9 = Excellent

[1/]From 10 different locations in the US

[2/]From 7 different locations in the US

TABLE 13

A Comparison of Winter Color, Fall Color, Genetic Color and Spring Greenup of 'Ba87-102' and Other Kentucky Bluegrass Varieties.

| Variety | Winter Color | Fall Color | Genetic Color | Spring Greenup |
|---|---|---|---|---|
| 'Ba87-102' | 4.8 | 6.3 | 6.4 | 5.5 |
| 'Abbey' | 5.0 | 6.0 | 6.4 | 5.6 |
| 'Ascot' | 4.5 | 7.3 | 7.1 | 5.1 |
| 'Coventry' | 4.7 | 5.7 | 6.4 | 5.6 |
| 'Chateau' | 5.0 | 6.3 | 6.2 | 5.6 |
| 'Classic' | 6.0 | 7.0 | 5.8 | 6.4 |
| 'Eclipse' | 5.3 | 7.0 | 6.5 | 5.6 |
| 'Glade' | 5.3 | 6.7 | 6.8 | 5.7 |
| 'Kenblue' | 5.3 | 5.3 | 5.4 | 6.2 |
| 'Limousine' | 4.3 | 5.3 | 6.3 | 5.5 |
| 'Midnight' | 5.7 | 7.7 | 7.7 | 5.6 |
| 'Raven' | 4.5 | 6.0 | 6.2 | 5.6 |
| 'Sidekick' | 5.2 | 6.3 | 6.3 | 5.5 |
| LSD (.05) | 0.8 | 0.9 | 0.2 | 0.3 |

Rating Scale: 0–9, 9 = Dark Green

TABLE 14

A Comparison of Turf Density of 'Ba87-102' and Other Kentucky Bluegrass Varieties.

| Variety | Turf Density Spring | Summer | Fall |
|---|---|---|---|
| 'Ba87-102' | 5.9 | 6.5 | 6.5 |
| 'Abbey' | 6.0 | 6.4 | 6.4 |

TABLE 14-continued

A Comparison of Turf Density of 'Ba87-102' and Other Kentucky Bluegrass Varieties.

| Variety | Turf Density Spring | Summer | Fall |
|---|---|---|---|
| 'Ascot' | 5.7 | 6.5 | 6.6 |
| 'Coventry' | 6.1 | 6.5 | 7.0 |
| 'Chateau' | 6.1 | 6.8 | 6.8 |
| 'Classic' | 6.2 | 7.0 | 6.9 |
| 'Eclipse' | 5.8 | 6.5 | 6.7 |
| 'Glade' | 6.4 | 6.8 | 7.0 |
| 'Kenblue' | 5.8 | 6.5 | 6.5 |
| 'Limousine' | 6.7 | 7.0 | 7.3 |
| 'Midnight' | 6.3 | 6.7 | 7.0 |
| 'Raven' | 6.1 | 6.7 | 6.3 |
| 'Sidekick' | 5.3 | 6.1 | 6.2 |
| LSD (.05) | 0.4 | NS | 0.3 |

Rating: 1–9; 9 = maximum density

TABLE 15

A Comparison of Leaf Texture of 'Ba87-102' and Other Kentucky Bluegrass Varieties

| Variety | Leaf Texture |
|---|---|
| 'Ba87-102' | 6.0 |
| 'Abbey' | 5.7 |
| 'Ascot' | 6.1 |
| 'Coventry' | 5.6 |
| 'Chateau' | 5.5 |
| 'Classic' | 6.2 |
| 'Eclipse' | 6.1 |
| 'Glade' | 6.6 |
| 'Kenblue' | 7.0 |
| 'Limousine' | 7.3 |
| 'Midnight' | 6.4 |
| 'Raven' | 5.6 |
| 'Sidekick' | 5.0 |
| LSD (.05) | 0.2 |

Rating: 1–9; 9 = Fine texture

Turf diseases are one of the major causes of inconsistent and poor turf performance. 'Ba87-102' has been found to have a good level of resistance to the following diseases: (1) Crown rust caused by *Puccinia coronata,* (2) Summer patch caused by *Magnaporthe poae,* (3) Powdery mildew caused by *Erysiphe graminis,* (4) Melting out caused by *Drechslera poae* (formerly *Helminthosporium vagans*), and (5) Brown patch caused by *Rhizoctonia solani.* This level of resistance is comparable to many of the improved varieties of Kentucky bluegrass.

Comparisons of disease incidence of 'Ba87-102' as compared with other Kentucky bluegrass varieties in regard to crown rust, summer patch, powdery mildew, melting out and brown patch are presented in Table 16 as follows:

TABLE 16

A Comparison of Crown Rust, Summer Patch, Powdery Mildew, Melting Out and Brown Patch Incidence of 'Ba87-102' and Other Kentucky Bluegrass Varieties.

| Variety | Crown Rust | Summer Patch | Powdery Mildew | Melting Out | Brown Patch |
|---|---|---|---|---|---|
| 'Ba87-102' | 9.0 | 7.5 | 7.0 | 5.3 | 5.0 |
| 'Abbey' | 9.0 | 7.8 | 6.7 | 6.0 | 3.8 |
| 'Ascot' | 8.0 | 6.5 | 8.7 | 8.0 | 6.7 |
| 'Coventry' | 8.7 | 7.8 | 8.7 | 7.0 | 6.8 |
| 'Chateau' | 9.0 | 7.0 | 8.7 | 7.0 | 4.7 |
| 'Classic' | 9.0 | 8.0 | 8.3 | 6.3 | 5.3 |

TABLE 16-continued

A Comparison of Crown Rust, Summer Patch, Powdery Mildew, Melting Out and Brown Patch Incidence of 'Ba87-102' and Other Kentucky Bluegrass Varieties.

| Variety | Crown Rust | Summer Patch | Powdery Mildew | Melting Out | Brown Patch |
|---|---|---|---|---|---|
| 'Eclipse' | 8.7 | 8.8 | 8.7 | 7.0 | 6.5 |
| 'Glade' | 9.0 | 7.5 | 6.7 | 7.2 | 4.8 |
| 'Kenblue' | 8.0 | 5.7 | 8.3 | 1.3 | 2.8 |
| 'Limousine' | 8.7 | 7.5 | 8.7 | 7.7 | 5.7 |
| 'Midnight' | 9.0 | 7.3 | 5.3 | 7.8 | 7.2 |
| 'Raven' | 9.0 | 6.8 | 6.7 | 6.5 | 4.8 |
| 'Sidekick' | 8.7 | 7.7 | 8.0 | 4.5 | 3.3 |
| LSD (.05) | 1.4 | 1.5 | 1.4 | 1.1 | 2.3 |

*Rating Scale: 0–9, 9 = No Disease

Seed yield is an important economic trait in Kentucky bluegrass since it directly affects production costs. Comparisons of the seed yield potential of 'Ba87-102' as compared with other Kentucky bluegrass varieties are presented in Table 17 as follows:

TABLE 17

A Comparison of Seed Yields of 'Ba87-102' and Other Kentucky Bluegrass Varieties at Connell, Washington.

| | Seed Yield (Lb./acre) |
|---|---|
| 'Ba87-102' | 1319 |
| 'Abbey' | 1493 |
| 'Allure' | 895 |

TABLE 17-continued

A Comparison of Seed Yields of 'Ba87-102' and Other Kentucky Bluegrass Varieties at Connell, Washington.

| | Seed Yield (Lb./acre) |
|---|---|
| 'Cobalt' | 857 |
| 'Sidekick' | 880 |
| LSD.05 | 268 |

What is claimed is:

1. A variety of Kentucky bluegrass, substantially as shown and described herein.

* * * * *